United States Patent
Revenkova et al.

(10) Patent No.: US 6,566,511 B2
(45) Date of Patent: May 20, 2003

(54) MAP KINASE PHOSPHATASE MUTANT

(75) Inventors: Ekaterina Revenkova, Fort Lee, NJ (US); Jurek Paszkowski, Del Mar, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/770,595

(22) Filed: Jan. 26, 2001

(65) Prior Publication Data

US 2002/0048803 A1 Apr. 25, 2002

Related U.S. Application Data

(63) Continuation of application No. PCT/EP99/05413, filed on Jul. 28, 1999.

(51) Int. Cl.$^7$ .......................... C07H 21/04; C12N 9/16; C12N 15/00; C12N 1/12; C12Q 1/68
(52) U.S. Cl. .................... 536/23.2; 435/196; 435/320.1; 435/252.3; 435/6
(58) Field of Search ............................... 536/23.2, 23.1; 435/196, 252.3, 320.1, 6

(56) References Cited

PUBLICATIONS

Misra–Press et al., J.B.C., 270, 14587–14596, 1995.*
Barford, D., *Molecular Mechanisms if the Protein Serine/Theonine Phosphatases Trends in Biochemical Sciences*, vol. 21 (Nov. 1996), pp. 407–412.
Bouchez et al, *Kanamycin Rescue: A Simple Technique for the Recovery of T–DNA Flanking Sequences Plant Molecular Biology Reporter*, vol. 14(2) (1996), pp. 115–123.
Dellaporta et al, *A Plant DNA Minipreparation: Version II Plant Molecular Biology Reporter*, vol. 1 (1983), pp. 19–21.
Denu et al, *Form and Function in Protein Dephosphorylation Cell*, vol. 87 (Nov. 1, 1996), pp. 361–364.
Fauman, E.B. and Saper, M.A., *Structure and function of the protein tyrosine phosphatases Trends in Biochemical Sciences*, vol. 21 (Nov. 1996) pp. 413–417.
Lewis et al, XCL 100, an inducible nuclear MAP kinase phosphatase from *Xenopus laevis*: its role in MAP kinase inactivation in differentiated cells and its expression during early development *Journal of Cell Science*, vol. 108, (1995) pp. 2885–2896.
Liu et al, Role of Mitogen–Activated Protein Kinase Phosphatase During the Cellular Responses to Genotoxic Stress *The Journal of Biological Chemistry*, vol. 270, No. 15 (Apr. 14, 1995), pp. 8377–8380.
Masson et al, *Mutants of Arabidopsis thaliana Hypersensitive to DNA–Damaging Treatments Genetics*, vol. 149 (1997), pp. 401–407.
Sun et al, *MKP–1 (3CH134), an Immediate Early Gene Product, Is a Duel Specificity Phosphatase That Dephosphorylates MAP Kinase In Vivo Cell*, vol. 75 (1993), pp. 487–493.
Tonks, N.K. and Neel, B.G., *From Form to Function: Signaling by Protein Tyrosine Phosphatases Cell*, vol. 87, (Nov. 1, 1996), pp. 365–368.
Van Vactor et al, *Genetic Analysis of Protein Tyrosine Phospjatases Current Opinion in Genetics & Development*, vol. 8 (1998), pp. 112–126.

\* cited by examiner

*Primary Examiner*—M. Monshipouri
(74) *Attorney, Agent, or Firm*—Marcia R. Morton; Randee S. Schwartz

(57) ABSTRACT

The present invention relates to DNA encoding proteins contributing to the regulation of a plant's response to DNA damage. DNA according to the invention comprises an open reading frame encoding a protein characterized by a stretch of amino acids or component amino acid sequence having 40% or more identity with an aligned component sequence of SEQ ID NO: 3. Preferably the DNA encodes a MAP kinase phosphatase.

14 Claims, No Drawings

SEQUENCE LISTING

<160> NUMBER OF SEQ ID NOS: 26

<210> SEQ ID NO 1
<211> LENGTH: 6356
<212> TYPE: DNA
<213> ORGANISM: Arabidopsis thaliana
<220> FEATURE:
<221> NAME/KEY: misc_feature
<222> LOCATION: (1)..(6356)
<223> OTHER INFORMATION: n = a, t, c, or g

<400> SEQUENCE: 1

```
gttcaaggtg gtgttatttn cagtattaga aaagaggctt ctagagagag tttctaaatt    60
atattttgaa cacggccgga ttggttgtct tatgattaag tgaatgcttt agatctggtg   120
acgattggta tatgagatat atagtanaat gatagaacat cagaaatact ataagtcacc   180
atatttttaa aaaataaatg ctatagaatt tttgttttgg taattgttat aactctacaa   240
agttatgtgt tatagagttt tactagtttc atcgttatca tgtgtatagt ataacncaac   300
aaaagaaatt ttaaatatct gaaaacataa aaatttaata aaatgatgtg agtataagaa   360 aaaagaaag aaagaaacaa cgtaaaaaat aaaaatcatt catacatata acaattttca   420
aaagatcaat gttaacttta attagtctttt tttcttatgt ttcatgcaaa tgcaatagta   480
ttacttttct ttaatctaag attatgtgtt gcttttaagc aagaactatt caaagagtca   540
aagacatgca tgtaaacttt agagaacggg atctttcatc aatcttattt tttttccttt   600
tttttttaca acgaacgata ggtagtaagc atgaatctgg ttcaaagttt ggatcagtgt   660
gggcataatc ctggttcgct aaaaagaatc aatataatat atgttgagcg taagagaaga   720
```

-continued

```
aagctcatag ttctgtgtag aaaaaacgtg gagattggag agaaattact aagagagcga  780
agagaagagt aaacctagaa gatacaaaag acgctatcaa aagattgttt tatgtgttta  840
tgaaacattc acttaggcca gtataaatat taaatgtcat tttgagaaag aaaaaaaaat  900
ggtgtcattt tgaggatata aatattttct caacaagatg ttttagactt tcaacataac  960
gatcatttaa aactacataa tttatctctt cgttaaaaac ttaacattaa caaaaagtta 1020
aattcgacaa gaagagttta ttcaataagt atactgtatg tgtttatttt attcacatga 1080
aaagtgtcaa acaacacttg ggatacatat ttcatgccta aaaatcgtat aacaacattt 1140
aaggtaatca gtaaatttga tgcctaaact aaaatatgtg accatttga ccaatgagca 1200 ttttttggaa ataaaactac tgcatacgac ctggtcaaac acatgaactg ccactgcttt 1260
taaaactacc ttttaaact tttgacgtcc attttattt actaattatt atgttaatca 1320
aaccactaac attatgattc gaatttcga gtgatgattg ttagaagtga tgtgaatgat 1380
gcggtataaa acaaattgtg atatatattc actcatatat atcaaaatca aatagctta 1440 tcgttccaaa acatgattga taaaatgtaa ttactattca aaacttaaag ccagtagtta 1500
aaataaaaca aaataaatag tatatgtttc atattaatgc ccaaccaata ttttgttttg 1560
atgaggaaaa gtctttttt tttttctctt ttttttctca tagttaaaag acataaaaaa 1620
aattaatatt acaaacaaga caaaaaaaaa gaataaaataa acaacaatc attactgtca 1680 aatcaattat cagagggaaa agttattaag aaatgtcaac caatgagtat cattatcatc 1740
atgctttttt agacccttct ttttaattca tcaagattta gtcttgttta taatttgaa 1800 gtaaaattct aaatgaatca attctacaat ttttccccta cattattgta acgataaaat 1860
ttaagatcaa caattacttc gttaatttt tttctgataa aaatatttga tatctttctg 1920
attatgatat attagcattg ttttgtatt gtatgtatgg taattaattt tagttcaaaa 1980
gaataataaa tggtttgatt agcatgaatt taataaaaaa ataagactga ataaacatag 2040
gtaataaact ttgtttctt tggtaaatgt aaaattagaa aaaatcataa tcccaaggta 2100
attactataa ttacattcaa tgtcagaatt aaacgtagtg aataaaaacc gtaaaacatg 2160
agaaaaacaa gaatttatta tctttgacaa gcaataaatg aaatgctgac aaaaaattgg 2220
tttcaaagtt tcaacgcgtt tcttataata agaattcaat ttcgtgcagc taatcaggag 2280
ataattatca taattaaatt aatcgttact actttataat actcccaaaa taatcgaaaa 2340
cgaatttatt ttattgtaat ttgtttaata ataagaatt actgtttcct cccacttccc 2400
atctctcttt tccttttgtg ttcttcttct tctccgcttt gtttccccaa tctctctctt 2460
ctctctctct gaagaaaaat aaataaaaga tctaactttg acggctctct taatcttact 2520
cactccgtaa gttccaaatc tctctccttt actctcatat ctatatcgtc cgaacaaaac 2580
ccaggagaat tgcttcaccc cctttttggg tttttaatca ttttctcaga ttctcagttt 2640
ctgtttccgt cttctagatt ctgggttcag tttctgtttt gctcttattg aattttctta 2700
ttcattttgt gtttcggagt tattcatggt agctgaattt gttaattctg atgttgtttt 2760
gcgttttctt cttttctagt ttggctatgt cgtctttgat ctgatgctgg gttattctct 2820
ttccctctgt tttggtttct tttagggttt taagtcggaa tagactgatg ggagcttgat 2880
ggttattgtt agatcagatg tggatttaaa gccttcgctg aactaacaag tctatggaag 2940
aagcaaagac ccttgtttta cactgtatgt tgtgaggaat tgtctgatt tgggtgata  3000 aaggtgaagt ctttgagttt gtaattttga gataagattg atggtgggga agagaggatg 3060
cgatggggaa tgatgaagct cctcctggtt ctaagaaaat gttttggcgg tctgcctctt 3120
```

```
ggtctgcttc acggactgca tcacaagttc ctgagggtga tgagcaaagc ctgaacattc  3180
cgtgtgctat tagttctggg ccgagtcgaa gatgtccagc tgctcctttg acacctcgtt  3240
cacatcataa cagcaaggct agagcttgtt tgccaccatt gcagcctctt gccatttcta  3300
ggaggagctt agacgagtgg cctaaggcgg gttcggatga tgtcggtgag tggcctcatc  3360
caccaacacc tagcgggaac aaaaccgggg agagattgaa gctcgattta tcatcaacgc  3420
agcagcgggt aacagataag agctctggtc tagctaagag ggagaagatt gctttctttg  3480
ataaagaatg ttcaaaggtt gctgatcata tatatgtggg tggagatgct gtggcgaaag  3540
acaagagcat actgaaaaac aatggaatca cgcatatctt gaactgcgtt ggttttatct  3600
gtccggaata tttcaagtct gattttttgtt acagatcctt gtggttacag gatagtccgt  3660
cagaggatat agctagtatt ctgtacgatg tgtttgacta ctttgaagat gtgagggagc  3720 aaaagtggaag gatctttgtt cattgttgtc aaggggtttc acgatctacc tcgttggtaa  3780
tagcatatct gatgtggaga gaagggcaaa gttttgatga tgcatttcag tatgtgaagt  3840
ctgctagagg tattgctgat cctaacatgg gctttgcttg ccaattgtta caatgccaaa  3900
agagggttca tgcgttcccg cttagcccta cctccttact tagaatgtac aaaatgtctc  3960
cacactctcc ttatgaccct ttgcatcttg ttccaaaact gttgaatgat ccatgcccga  4020
gttctctgga ttcaagaggt gcatttatca ttcagttacc ttctgcaatt tacatttggg  4080
ttggtaggca gtgtgaaacc atcatggaga aagatgcaaa agctgctgtt tgtcagattg  4140
ctcgatatga gaaagtcgaa gcacctatta tggtggtcag agaaggtgat gagcctgttt  4200
attactggga tgcatttgca agcattttgc ctatgattgg gggctcggta attaaagttc  4260
aaccaggtga caggaaggtc gacgcatata atctggattt tgagattttt cagaaagcca  4320
tagagggagg ttttgtgcca actttagcat catccaacaa cgaacatgag actcatcttc  4380
ctgcaaggga aaacagttgg agctcactga aatgtaagtt tgcatcaagg tttgacaaag  4440
gttttcggta tgtctccaaa acgccactat ctagggtcta ttcagattcg atgatgatcg  4500
tgcattcatc aggctcacct tcctcaacaa cttcttcatc atccactgcg tcgcctcctt  4560
ttctctctcc cgattctgta tgttcaacaa attcaggcaa tagcttaaag agtttctctc  4620
aatcctctgg acgttcgtcc ttgagacctt ctattccacc atcgctgaca ttgcctaaat  4680
tttccagcct atccctcctc ccttcccaaa cttctcctaa agaatctcgt ggtgtcaata  4740
cttttcttca accgtcacca aatagaaagg cttcaccttc tcttgctgag cgtagaggca  4800
gcctgaaagg atctctgaag ttgccaggtt tggctgattc caacagaggc acacctgctt  4860
ttactttaca tccggatgat agtaatgaca tagtcttcaa tctggagggt attagaaacg  4920
gcgatctata tccaccaagt gattgcaaag ggacaagtgt agattcagat ttgccagaga  4980
aggaaattat atccttaatc agttgcagta aatctgacag acacaaatcg ggaggtgata  5040
ctgatagctc tggccagcct ttagcatgtc gttggccaag tatggagatg attacaaaac  5100
tgagcagagc ttacttagat tcagaatctg ttatagcaat cccgttgcca agtgatgctg  5160
taggagaaac gggtagtagg aatttgtaca tttggatcgg aaagtcattc tctttggata  5220
acaactgttc tctagtagat agcaacaaag cggcagacac tgtggagaat gttgattggg  5280
tacaaattgg tgaatccatt ttgtgtcaga tggacttgcc aaaagatacc cctataaagg  5340
taataatagc ctaaactttg gaggctctga tacttttttac taattgtaaa gtctgcgtgc  5400
tcatctttgt catgtcttat ccaaccaaac tatatttcga agatgaaaat tacaatctca  5460
```

-continued

```
gcactttcat tactgactac tgaggacggt taggtagaat ccttatgatt tcagcagttg 5520
tatgtattgg tttattctct agtggtttgc atggttccaa cttgttatga tccttttgtt 5580
gtttgtaact gataagttgc ttttcttcct tgttaacaga tagttaggga atctgaggat 5640
cagacagagt tgctagcact gctgagcgcg ctataacacc cacccgcaag ctctacacat 5700
ttactctgtt ttttttcac agattccttc aaccgcaaca cttttccatt ttcagacaga 5760
gtattcattc agctcaggtg agaattctct gaaagcagtc tgtaacactt catcttcaca 5820
gttgcatccg aatacaatcg ttagttctgg attatgttta attgctatct gatcatgaat 5880
ttgagttaga ggatggttgg aacaaaaaaa cttagaagct cgaatgaccg gttttttacca 5940 aattctcata gaccatattt gattcttttg atttacttct ggtgcaggac tctctgtgct 6000
tatggaagtt gatgttgggg gaaacaactc tcttgtacag tggggaaaaa acttcttctt 6060
cttctttcta tcacatgaaa atcctcaagg gccattatta gtatgatcag attataaaat 6120
tgtaaggtta ggggctttat gaggattttg atggacttgt acaatgtttt acatatacac 6180
tcagcagcac aatagatttt tgttaaactt acatgttatt caagtaaaag tactatgtag 6240
atgttgaagt ctaattgaag aattagttaa tgatagtctt aaacacttga ttcacttgtc 6300
atccaatttt ggttttgcgc atagtttctc ttcttttatt tcctctctaa aacacg      6356
```

<210> SEQ ID NO 2
<211> LENGTH: 3059
<212> TYPE: DNA
<213> ORGANISM: Arabidopsis thaliana

<400> SEQUENCE: 2

```
cttcttctcc gctttgtttc cccaatctct ctcttctctc tctctgaaga aaaataaata   60
aaagatctaa ctttgacggc tctcttaatc ttactcactc cggttttaag tcggaataga  120
ctgatgggag cttgatggtt attgttagat cagatgtgga tttaaagcct tcgctgaact  180
aacaagtcta tggaagaagc aaagacccct gttttacact gtatgttgtg aggaatttgt  240
ctgattttgg gtgataaagg tgaagtcttt gagtttgtaa ttttgagata agattggatg  300
gtgggaagag aggatgcgat ggggaatgat gaagctcctc ctggttctaa gaaaatgttt  360
tggcggtctg cctcttggtc tgcttcacgg actgcatcac aagttcctga gggtgatgag  420
caaagcctga acattccgtg tgctattagt tctgggccga gtcgaagatg tccagctgct  480
cctttgacac ctcgttcaca tcataacagc aaggctagac cttgtttgcc accattgcag  540
cctcttgcca tttctaggag gagcttagac gagtggccta aggcgggttc ggatgatgtc  600
ggtgagtggc ctcatccacc aacacctagc gggaacaaaa ccggggagag attgaagctc  660
gatttatcat caacgcagca gcgggtaaca gataagagct ctggtctagc taagagggag  720
aagattgctt tctttgataa agaatgttca aaggttgctg atcatatata tgtgggtgga  780
gatgctgtgg cgaaagacaa gagcatactg aaaaacaatg gaatcacgca tatcttgaac  840
tgcgttggtt ttatctgtcc ggaatatttc aagtctgatt tttgttacag atccttgtgg  900
ttacaggata gtccgtcaga ggatataact agtattctgt acgatgtgtt tgactacttt  960
gaagatgtga gggagcaaag tggaaggatc tttgttcatt gttgtcaagg ggtttcacga 1020
tctacctcgt tggtaatagc atatctgatg tggagagaag ggcaaagttt tgatgatgca 1080
tttcagtatg tgaagtctgc tagaggtatt gctgatccta acatgggctt gcttgccaa  1140 ttgttacaat gccaaaagag ggttcatgcg ttcccgctta gccctacctc cttacttaga 1200
atgtacaaaa tgtctccaca ctctccttat gacccttttgc atcttgttcc aaaactgttg 1260
```

```
aatgatccat gcccgggttc tctggattca agaggtgcat ttatcattca gttaccttct 1320
gcaatttaca tttgggttgg taggcagtgt gaaaccatca tggagaaaga tgcaaaagct 1380
gctgtttgtc agattgctcg atatgagaaa gtcgaagcac ctattatggt ggtcagagaa 1440
ggtgatgagc ctgtttatta ctgggatgca tttgcaagca ttttgcctat gattgggggc 1500
tcggtaatta aagttcaacc aggtgacagg aaggtcgacg catataatct ggattttgag 1560 attttttcaga aagccataga gggaggtttt gtgccaactt tagcatcatc caacaacgaa 1620
catgagactc atcttcctgc aagggaaaac agttggagct cactgaaatg taagtttgca 1680
tcaaggtttg acaaaggttt tcggtatgtc tccaaaacgc cactatctag ggtctattca 1740
gattcgatga tgatcgtgca ttcatcaggc tcaccttcct caacaacttc ttcatcatcc 1800
actgcgtcgc ctcctttct ctctcccgat tctgtatgtt caacaaattc aggcaatagc 1860
ttaaagagtt tctctcaatc ctctggacgt tcgtccttga accttctat tccaccatcg 1920 ctgacattgc ctaaatttc cagcctatcc ctcctcccttt cccaaacttc tcctaaagaa 1980
tctcgtggtg tcaatacttt tcttcaaccg tcaccaaata gaaaggcttc accttctctt 2040
gctgagcgta gaggcagcct gaaaggatct ctgaagttgc caggtttggc tgattccaac 2100
agaggcacac ctgcttttac tttacatccg gatgatagta atgacatagt cttcaatctg 2160
gagggtatta gaaacggcga tctatatcca ccaagtgatt gcaaagggac aagtgtagat 2220
tcagatttgc cagagaagga aattatatcc ttaatcagtt gcagtaaatc tgacagacac 2280
aaatcgggag gtgatactga tagctctggc cagccttag catgtcgttg gccaagtatg 2340
gagatgatta caaaactgag cagagcttac ttagattcag aatctgttat agcaatcccg 2400
ttgccaagtg atgctgtagg agaaacgggt agtaggaatt tgtacatttg gatcggaaag 2460
tcattctctt tggataacaa ctgttctcta gtagatagca acaaagcggc agacactgtg 2520
gagaatgttg attgggtaca aattggtgaa tccatttgt gtcagatgga cttgccaaaa 2580
gataccccta taaagatagt tagggaatct gaggatcaga cagagttgct agcactgctg 2640
agcgcgctat aacacccacc cgcaagctct acacatttac tctgttttt tttcacagat 2700 tccttcaacc gcaacacttt tccatttca gacagagtat tcattcagct caggactctc 2760
tgtgcttatg gaagttgatg ttgggggaaa caactctctt gtacagtggg gaaaaaactt 2820
cttcttcttc tttctatcac atgaaaatcc tcaagggcca ttattagtat gatcagatta 2880
taaaattgta aggttagggg cttttatgagg attttgatgg acttgttaca atgtttacat 2940
atacactcag cagcacaata gatttttgtt aaacttacat gttattcaag taaaagtact 3000
atgtagatgt tgaagtctaa ttgaagaatt agttaatgat aaaaaaaaaa aaaaaaaa  3059
```

<210> SEQ ID NO 3
<211> LENGTH: 784
<212> TYPE: PRT
<213> ORGANISM: Arabidopsis thaliana

<400> SEQUENCE: 3

```
Met Val Gly Arg Glu Asp Ala Met Gly Asn Asp Glu Ala Pro Pro Gly
1               5                   10                  15

Ser Lys Lys Met Phe Trp Arg Ser Ala Ser Trp Ser Ala Ser Arg Thr
            20                  25                  30

Ala Ser Gln Val Pro Glu Gly Asp Glu Gln Ser Leu Asn Ile Pro Cys
        35                  40                  45

Ala Ile Ser Ser Gly Pro Ser Arg Arg Cys Pro Ala Ala Pro Leu Thr
```

```
              50                  55                  60
Pro Arg Ser His His Asn Ser Lys Ala Arg Ala Cys Leu Pro Pro Leu
 65                  70                  75                  80

Gln Pro Leu Ala Ile Ser Arg Arg Ser Leu Asp Glu Trp Pro Lys Ala
                 85                  90                  95

Gly Ser Asp Asp Val Gly Glu Trp Pro His Pro Pro Thr Pro Ser Gly
                100                 105                 110

Asn Lys Thr Gly Glu Arg Leu Lys Leu Asp Leu Ser Ser Thr Gln Gln
                115                 120                 125

Arg Val Thr Asp Lys Ser Ser Gly Leu Ala Lys Arg Glu Lys Ile Ala
                130                 135                 140

Phe Phe Asp Lys Glu Cys Ser Lys Val Ala Asp His Ile Tyr Val Gly
145                 150                 155                 160

Gly Asp Ala Val Ala Lys Asp Lys Ser Ile Leu Lys Asn Asn Gly Ile
                165                 170                 175

Thr His Ile Leu Asn Cys Val Gly Phe Ile Cys Pro Glu Tyr Phe Lys
                180                 185                 190

Ser Asp Phe Cys Tyr Arg Ser Leu Trp Leu Gln Asp Ser Pro Ser Glu
                195                 200                 205

Asp Ile Thr Ser Ile Leu Tyr Asp Val Phe Asp Tyr Phe Glu Asp Val
                210                 215                 220

Arg Glu Gln Ser Gly Arg Ile Phe Val His Cys Cys Gln Gly Val Ser
225                 230                 235                 240

Arg Ser Thr Ser Leu Val Ile Ala Tyr Leu Met Trp Arg Glu Gly Gln
                245                 250                 255

Ser Phe Asp Asp Ala Phe Gln Tyr Val Lys Ser Ala Arg Gly Ile Ala
                260                 265                 270

Asp Pro Asn Met Gly Phe Ala Cys Gln Leu Leu Gln Cys Gln Lys Arg
                275                 280                 285

Val His Ala Phe Pro Leu Ser Pro Thr Ser Leu Leu Arg Met Tyr Lys
                290                 295                 300

Met Ser Pro His Ser Pro Tyr Asp Pro Leu His Leu Val Pro Lys Leu
305                 310                 315                 320

Leu Asn Asp Pro Cys Pro Gly Ser Leu Asp Ser Arg Gly Ala Phe Ile
                325                 330                 335

Ile Gln Leu Pro Ser Ala Ile Tyr Ile Trp Val Gly Arg Gln Cys Glu
                340                 345                 350

Thr Ile Met Glu Lys Asp Ala Lys Ala Val Cys Gln Ile Ala Arg
                355                 360                 365

Tyr Glu Lys Val Glu Ala Pro Ile Met Val Val Arg Glu Gly Asp Glu
                370                 375                 380

Pro Val Tyr Tyr Trp Asp Ala Phe Ala Ser Ile Leu Pro Met Ile Gly
385                 390                 395                 400

Gly Ser Val Ile Lys Val Gln Pro Gly Asp Arg Lys Val Asp Ala Tyr
                405                 410                 415

Asn Leu Asp Phe Glu Ile Phe Gln Lys Ala Ile Glu Gly Gly Phe Val
                420                 425                 430

Pro Thr Leu Ala Ser Ser Asn Asn Glu His Glu Thr His Leu Pro Ala
                435                 440                 445

Arg Glu Asn Ser Trp Ser Ser Leu Lys Cys Lys Phe Ala Ser Arg Phe
                450                 455                 460

Asp Lys Gly Phe Arg Tyr Val Ser Lys Thr Pro Leu Ser Arg Val Tyr
465                 470                 475                 480
```

```
Ser Asp Ser Met Met Ile Val His Ser Ser Gly Ser Pro Ser Ser Thr
            485                 490                 495
Thr Ser Ser Ser Ser Thr Ala Ser Pro Pro Phe Leu Ser Pro Asp Ser
            500                 505                 510
Val Cys Ser Thr Asn Ser Gly Asn Ser Leu Lys Ser Phe Ser Gln Ser
            515                 520                 525
Ser Gly Arg Ser Ser Leu Arg Pro Ser Ile Pro Pro Ser Leu Thr Leu
            530                 535                 540
Pro Lys Phe Ser Ser Leu Ser Leu Leu Pro Ser Gln Thr Ser Pro Lys
545                 550                 555                 560
Glu Ser Arg Gly Val Asn Thr Phe Leu Gln Pro Ser Pro Asn Arg Lys
            565                 570                 575
Ala Ser Pro Ser Leu Ala Glu Arg Arg Gly Ser Leu Lys Gly Ser Leu
            580                 585                 590
Lys Leu Pro Gly Leu Ala Asp Ser Asn Arg Gly Thr Pro Ala Phe Thr
            595                 600                 605
Leu His Pro Asp Asp Ser Asn Asp Ile Val Phe Asn Leu Glu Gly Ile
            610                 615                 620
Arg Asn Gly Asp Leu Tyr Pro Pro Ser Asp Cys Lys Gly Thr Ser Val
625                 630                 635                 640
Asp Ser Asp Leu Pro Glu Lys Glu Ile Ile Ser Leu Ile Ser Cys Ser
            645                 650                 655
Lys Ser Asp Arg His Lys Ser Gly Gly Asp Thr Asp Ser Ser Gly Gln
            660                 665                 670
Pro Leu Ala Cys Arg Trp Pro Ser Met Glu Met Ile Thr Lys Leu Ser
            675                 680                 685
Arg Ala Tyr Leu Asp Ser Glu Ser Val Ile Ala Ile Pro Leu Pro Ser
690                 695                 700
Asp Ala Val Gly Glu Thr Gly Ser Arg Asn Leu Tyr Ile Trp Ile Gly
705                 710                 715                 720
Lys Ser Phe Ser Leu Asp Asn Asn Cys Ser Leu Val Asp Ser Asn Lys
            725                 730                 735
Ala Ala Asp Thr Val Glu Asn Val Asp Trp Val Gln Ile Gly Glu Ser
            740                 745                 750
Ile Leu Cys Gln Met Asp Leu Pro Lys Asp Thr Pro Ile Lys Ile Val
            755                 760                 765
Arg Glu Ser Glu Asp Gln Thr Glu Leu Leu Ala Leu Leu Ser Ala Leu
770                 775                 780

<210> SEQ ID NO 4
<211> LENGTH: 10
<212> TYPE: PRT
<213> ORGANISM: Arabidopsis thaliana

<400> SEQUENCE: 4

Val His Cys Cys Gln Gly Val Ser Arg Ser
 1               5                   10

<210> SEQ ID NO 5
<211> LENGTH: 10
<212> TYPE: PRT
<213> ORGANISM: Artificial Sequence
<220> FEATURE:
<221> MISC_FEATURE<222> (1)..(10)<223> Xaa = any amino acid
<223> OTHER INFORMATION: Description of Artificial Sequence: mammalian
      sequence motif defining the family of PTPs

<400> SEQUENCE: 5
```

```
Ile His Cys Xaa Ala Gly Xaa Xaa Arg Ser
  1               5                  10
```

<210> SEQ ID NO 6
<211> LENGTH: 14
<212> TYPE: PRT
<213> ORGANISM: Arabidopsis thaliana

<400> SEQUENCE: 6

```
Thr Ser Ile Leu Tyr Asp Val Phe Asp Tyr Phe Glu Asp Val
  1               5                  10
```

<210> SEQ ID NO 7
<211> LENGTH: 12
<212> TYPE: PRT
<213> ORGANISM: Arabidopsis thaliana

<400> SEQUENCE: 7

```
Phe Val His Cys Cys Gln Gly Val Ser Arg Ser Thr
  1               5                  10
```

<210> SEQ ID NO 8
<211> LENGTH: 4
<212> TYPE: PRT
<213> ORGANISM: Arabidopsis thaliana

<400> SEQUENCE: 8

```
Phe Val His Cys
  1
```

<210> SEQ ID NO 9
<211> LENGTH: 6
<212> TYPE: PRT
<213> ORGANISM: Arabidopsis thaliana

<400> SEQUENCE: 9

```
Gln Gly Val Ser Arg Ser
  1               5
```

<210> SEQ ID NO 10
<211> LENGTH: 5
<212> TYPE: PRT
<213> ORGANISM: Arabidopsis thaliana

<400> SEQUENCE: 10

```
Tyr Phe Lys Ser Asp
  1               5
```

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: degenerate
      primer
<221> NAME/KEY: misc_feature
<222> LOCATION: (1)..(23)
<223> OTHER INFORMATION: n = i

<400> SEQUENCE: 11
aayaayggna thacncayat hyt                                        23

<210> SEQ ID NO 12
<211> LENGTH: 24
<212> TYPE: DNA

```
<213> ORGANISM: Artificial Sequence
<220> FEATURE:
<223> OTHER INFORMATION: Description of Artificial Sequence: degenerate
      primer
<221> NAME/KEY: misc_feature
<222> LOCATION: (1)..(24)
<223> OTHER INFORMATION: n = i

<400> SEQUENCE: 12
ytgrcangcr aancccatrt tngg                                              24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: degenerate
      primer
<221> NAME/KEY: misc_feature
<222> LOCATION: (1)..(24)
<223> OTHER INFORMATION: n = i

<400> SEQUENCE: 13
ngtccacatn arrtangcda tnac                                              24

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 14
ggtttctaca ggacgtaaca t                                                 21

<210> SEQ ID NO 15
<211> LENGTH: 196
<212> TYPE: DNA
<213> ORGANISM: Sinapis alba

<400> SEQUENCE: 15
caactgcgtt ggtttcatct gtcctgaata tttcaagtct gattttgtt accggtcgtt        60 gtggttacgt gatagtccat cagaggatat aactagcatt ctctacgatg tctttgacta     120
ctttgaagac gttagggagc aaagtgggag gatctttgtt cactgttgtc aaggcgtttc     180
acggtctacc tccttg                                                     196

<210> SEQ ID NO 16
<211> LENGTH: 65
<212> TYPE: PRT
<213> ORGANISM: Sinapis alba

<400> SEQUENCE: 16

Asn Cys Val Gly Phe Ile Cys Pro Glu Tyr Phe Lys Ser Asp Phe Cys
  1               5                  10                  15

Tyr Arg Ser Leu Trp Leu Arg Asp Ser Pro Ser Glu Asp Ile Thr Ser
             20                  25                  30

Ile Leu Tyr Asp Val Phe Asp Tyr Phe Glu Asp Val Arg Glu Gln Ser
         35                  40                  45

Gly Arg Ile Phe Val His Cys Cys Gln Gly Val Ser Arg Ser Thr Ser
     50                  55                  60

Leu
 65
```

<210> SEQ ID NO 17
<211> LENGTH: 196
<212> TYPE: DNA
<213> ORGANISM: Lycopersicon esculentum

<400> SEQUENCE: 17

```
aaactgtgta gggtttagtt gtcctgaata ctttaaggat gaccttgtat acaagacact    60
ttggctgcag gatagcccca ctgaggacat cacaagtatt ctttatgatg tctttgatta   120
ctttgaagat gttcatgaac aaggtgggag tgtctttgta cactgcttcc agggggtgtc   180
ccgatcagcc tccttg                                                   196
```

<210> SEQ ID NO 18
<211> LENGTH: 65
<212> TYPE: PRT
<213> ORGANISM: Lycopersicon esculentum

<400> SEQUENCE: 18

```
Asn Cys Val Gly Phe Ser Cys Pro Glu Tyr Phe Lys Asp Asp Leu Val
 1               5                  10                  15

Tyr Lys Thr Leu Trp Leu Gln Asp Ser Pro Thr Glu Asp Ile Thr Ser
             20                  25                  30

Ile Leu Tyr Asp Val Phe Asp Tyr Phe Glu Asp Val His Glu Gln Gly
         35                  40                  45

Gly Ser Val Phe Val His Cys Phe Gln Gly Val Ser Arg Ser Ala Ser
     50                  55                  60

Leu
 65
```

<210> SEQ ID NO 19
<211> LENGTH: 196
<212> TYPE: DNA
<213> ORGANISM: Zea mays

<400> SEQUENCE: 19

```
caactgcatg ggcttcgtct gcccgaagta cttcaagtct gaccttgtct accgcaccct    60
ctggctgcag gacagcccca ccgaggacac caccagcatc ctttacgacg tgtttgatta   120
ctttgaggac gtcagggagc aggtggccg cgtgtttgtg cattgctgcc agggggtgtc    180
gcgctccacg cctctg                                                   196
```

<210> SEQ ID NO 20
<211> LENGTH: 65
<212> TYPE: PRT
<213> ORGANISM: Zea mays

<400> SEQUENCE: 20

```
Asn Cys Met Gly Phe Val Cys Pro Lys Tyr Phe Lys Ser Asp Leu Val
 1               5                  10                  15

Tyr Arg Thr Leu Trp Leu Gln Asp Ser Pro Thr Glu Asp Thr Thr Ser
             20                  25                  30

Ile Leu Tyr Asp Val Phe Asp Tyr Phe Glu Asp Val Arg Glu Gln Gly
         35                  40                  45

Gly Arg Val Phe Val His Cys Cys Gln Gly Val Ser Arg Ser Thr Pro
     50                  55                  60

Leu
 65
```

<210> SEQ ID NO 21
<211> LENGTH: 2450
<212> TYPE: DNA
<213> ORGANISM: Zea mays

<400> SEQUENCE: 21

```
ggcgggtcct cccccgccaa gcccggggag gggctccgcc tcgacctctc ctcgctccgg    60
tcgcagggc gcaaggacca gatcgccttc ttcgacaagg agtgctccaa ggtcgccgac   120
cacgtctacc tcggcggcga cgccgtcgcc aagaaccgcg acatcctcag gaagaacggc   180
atcacccacg tgctcaactg tgtgggcttt gtctgcccgg agtacttcaa gtcggaccta   240
gtctaccgca ccctctggct gcaggacagc cccaccgagg acatcaccag catcctgtac   300
gacgtgtttg actacttcga ggacgtcagg gagcagggcc gccgcgtgct tgtgcattgc   360
tgccaggggg tgtcacgctc cacgtcgctg gtcatcgcct acttgatgtg gagggaaggc   420
cagagcttcg atgacgcctt ccagtttgtc aaggctgccc ggggatcgc aaatccaaac   480
atgggctttg catgccagct tctccagtgc agaagcgtg tgcatgcgat tccgctgtca   540
ccaaattcag tgctcaggat gtaccgcatg gcgcctcact cccagtatgc ccctctgcat   600
ttggtgccca aaatgctcaa tgacccatcc ccagccaccc ttgactctag aggcgcgttc   660
attgtgcatg ttctctcgtc gctctatgtc tgggttggaa tgaagtgtga tccgtaatg   720
gaaaaggatg caaaggctgc tgcgtttcag gtagtgaggt atgagaaggt gcaggggcac   780
atcaaggttg tgagagaagg tctggagccg caggagttct gggatgcatt ttcaagtatg   840
ccacctaatt cagatagtaa tacaaagatt agcaaggacc agatcgattc agcatccaag   900
agtgacccag gaagccggaa aaatgagtcc tatgacgctg attttgagct tgtctacaaa   960
gcaatcactg ggggagtggt ccctgcattt tcaacttctg gggctggtga tgagacccat  1020
cttccagcta gagaaagtag ctggagttta ctgaggcaca gtttatctc caggtcgcta  1080
gctcgtgttt attcagattc tgctctaatg aaggattttg atccacgggt acaacacctg  1140
gctgctgagg catcaacctc acctcctttc ctttctccaa gctccttatc atcggattca  1200
agtgtcagct cgaagtatag ttcagactca ccctccttat cacctacaac tggctctcca  1260
ccatcatttg gcctctcgcc tgcttcatct aatctgacac atgctttggt gccatcatcc  1320
aggtctcccc tttctcaatc atctaatgaa ggagcttcaa agccttctgg catggaatca  1380
atacactctc cttccaagac ctcttctata gcagaaagga gaggaggctt cacacttcta  1440
aagctaccat ctctccaaaa ggatcttgta ttgccaccaa gggtgccgtc tattgtattg  1500
ccaccaaggg cgccatctag tattcgcagg accgaggatg cctcagataa tagtacaaat  1560
ggggttaaac agctgactag tgagttttgc tcagaaaaat gcactggtaa tagtttgagc  1620
tcgcattctg aaactagatt aattgagcgt actgacagta actcagaagt ctgcagtaat  1680
gcacaacttg tagtctacca gtggcccagc atgggaaagc taactacatt tgcacgcaag  1740
gatcttgacc cgaagtcggt tttaattttt gttacttcga atgccatcag gagaggagaa  1800
gcagttaaaa tggtgtatgt atgggtagga ggcgaaaatg agagcagcaa gagtgttgac  1860
tccgtcgatt ggcaacaggt cactagtgat tttcttcatc taaagggcct cagcaatgtt  1920
cttcctgtca aggtttcaa ggagcatgaa gctgagaatc ttttggaact actgaatgtt  1980
agttaacatt aggcagtagc tatcaggata attgtagttg ctaaacaaac tcaacgaagg  2040
catgccctcc agcatcagtc ggtaccgatg attgtcagcg aggtataaag ccacagccat  2100
tcccttgaac ataataagct acaaacagat tccgttctgc aactgcgcct catgatctat  2160
```

-continued

```
attttgtcca gatggcagga ggctgccatg ggcgttgtat cggttgcgaa ttagcactcg   2220
tggtgtagga gcaatcggcc gattcggtgt atattatccg ctcccctgta atgtaagctc   2280
agatactggg agctggtgtg tcgacagtta cttttttagcc taaacattct tgtacatctt  2340
tgaaaggaac agagttgtaa tccttttgac tatgtaaatg gctccattgg tcataacttc   2400
taaaccatgt ggaactcagt tgctagctgg taaaaaaaaa aaaaaaaaa                2450
```

<210> SEQ ID NO 22
<211> LENGTH: 661
<212> TYPE: PRT
<213> ORGANISM: Zea mays

<400> SEQUENCE: 22

```
Gly Gly Ser Ser Pro Ala Lys Pro Gly Glu Gly Leu Arg Leu Asp Leu
 1               5                  10                  15

Ser Ser Leu Arg Ser Gln Gly Arg Lys Asp Gln Ile Ala Phe Phe Asp
             20                  25                  30

Lys Glu Cys Ser Lys Val Ala Asp His Val Tyr Leu Gly Gly Asp Ala
         35                  40                  45

Val Ala Lys Asn Arg Asp Ile Leu Arg Lys Asn Gly Ile Thr His Val
     50                  55                  60

Leu Asn Cys Val Gly Phe Val Cys Pro Glu Tyr Phe Lys Ser Asp Leu
 65                  70                  75                  80

Val Tyr Arg Thr Leu Trp Leu Gln Asp Ser Pro Thr Glu Asp Ile Thr
                 85                  90                  95

Ser Ile Leu Tyr Asp Val Phe Asp Tyr Phe Glu Asp Val Arg Glu Gln
            100                 105                 110

Gly Gly Arg Val Leu Val His Cys Cys Gln Gly Val Ser Arg Ser Thr
        115                 120                 125

Ser Leu Val Ile Ala Tyr Leu Met Trp Arg Glu Gly Gln Ser Phe Asp
    130                 135                 140

Asp Ala Phe Gln Phe Val Lys Ala Ala Arg Gly Ile Ala Asn Pro Asn
145                 150                 155                 160

Met Gly Phe Ala Cys Gln Leu Leu Gln Cys Gln Lys Arg Val His Ala
                165                 170                 175

Ile Pro Leu Ser Pro Asn Ser Val Leu Arg Met Tyr Arg Met Ala Pro
            180                 185                 190

His Ser Gln Tyr Ala Pro Leu His Leu Val Pro Lys Met Leu Asn Asp
        195                 200                 205

Pro Ser Pro Ala Thr Leu Asp Ser Arg Gly Ala Phe Ile Val His Val
    210                 215                 220

Leu Ser Ser Leu Tyr Val Trp Val Gly Met Lys Cys Asp Pro Val Met
225                 230                 235                 240

Glu Lys Asp Ala Lys Ala Ala Phe Gln Val Val Arg Tyr Glu Lys
                245                 250                 255

Val Gln Gly His Ile Lys Val Val Arg Glu Gly Leu Glu Pro Gln Glu
            260                 265                 270

Phe Trp Asp Ala Phe Ser Ser Met Pro Pro Asn Ser Asp Ser Asn Thr
        275                 280                 285

Lys Ile Ser Lys Asp Gln Ile Asp Ser Ala Ser Lys Ser Asp Pro Gly
    290                 295                 300

Ser Arg Lys Asn Glu Ser Tyr Asp Ala Asp Phe Glu Leu Val Tyr Lys
305                 310                 315                 320

Ala Ile Thr Gly Gly Val Val Pro Ala Phe Ser Thr Ser Gly Ala Gly
```

|     |     |     |     |     |     |     |     |     |     |     |
| --- | --- | --- | --- | --- | --- | --- | --- | --- | --- | --- |
|     |     | 325 |     |     |     | 330 |     |     |     | 335 |

Asp Glu Thr His Leu Pro Ala Arg Glu Ser Ser Trp Ser Leu Leu Arg
          340                 345                 350

His Lys Phe Ile Ser Arg Ser Leu Ala Arg Val Tyr Ser Asp Ser Ala
          355                 360                 365

Leu Met Lys Asp Phe Asp Pro Arg Val Gln His Leu Ala Ala Glu Ala
370                 375                 380

Ser Thr Ser Pro Pro Phe Leu Ser Pro Ser Ser Leu Ser Ser Asp Ser
385                 390                 395                 400

Ser Val Ser Ser Lys Tyr Ser Ser Asp Ser Pro Ser Leu Ser Pro Thr
              405                 410                 415

Thr Gly Ser Pro Pro Ser Phe Gly Leu Ser Pro Ala Ser Ser Asn Leu
              420                 425                 430

Thr His Ala Leu Val Pro Ser Ser Arg Ser Pro Leu Ser Gln Ser Ser
              435                 440                 445

Asn Glu Gly Ala Ser Lys Pro Ser Gly Met Glu Ser Ile His Ser Pro
450                 455                 460

Ser Lys Thr Ser Ser Ile Ala Glu Arg Arg Gly Gly Phe Thr Leu Leu
465                 470                 475                 480

Lys Leu Pro Ser Leu Gln Lys Asp Leu Val Leu Pro Pro Arg Val Pro
              485                 490                 495

Ser Ile Val Leu Pro Pro Arg Ala Pro Ser Ser Ile Arg Arg Thr Glu
              500                 505                 510

Asp Ala Ser Asp Asn Ser Thr Asn Gly Val Lys Gln Leu Thr Ser Glu
              515                 520                 525

Phe Cys Ser Glu Lys Cys Thr Gly Asn Ser Leu Ser Ser His Ser Glu
              530                 535                 540

Thr Arg Leu Ile Glu Arg Thr Asp Ser Asn Ser Glu Val Cys Ser Asn
545                 550                 555                 560

Ala Gln Leu Val Val Tyr Gln Trp Pro Ser Met Gly Lys Leu Thr Thr
              565                 570                 575

Phe Ala Arg Lys Asp Leu Asp Pro Lys Ser Val Leu Ile Phe Val Thr
              580                 585                 590

Ser Asn Ala Ile Arg Arg Gly Glu Ala Val Lys Met Val Tyr Val Trp
              595                 600                 605

Val Gly Gly Glu Asn Glu Ser Ser Lys Ser Val Asp Ser Val Asp Trp
610                 615                 620

Gln Gln Val Thr Ser Asp Phe Leu His Leu Lys Gly Leu Ser Asn Val
625                 630                 635                 640

Leu Pro Val Lys Val Phe Lys Glu His Glu Ala Glu Asn Leu Leu Glu
              645                 650                 655

Leu Leu Asn Val Ser
              660

<210> SEQ ID NO 23
<211> LENGTH: 522
<212> TYPE: DNA
<213> ORGANISM: Lycopersicon esculentum

<400> SEQUENCE: 23
aactgtgtgg ggtttgtatg cccagagtat ttcaagtctg atttcgtata ccggactttg    60
tggttgcagg atagcccatc agaagatatt actagtattc tctatgatgt ttttgactac   120
tttgaagatg tcagggagca acatgggaag gtttttgttc attgctgcca agggtctct   180

```
cggtcaacct cgttggttat tgcttatcgt atgtggagag aaggacaaag ttttgatgat    240
gcctttgagt atgtaaaggc agcaaggggt attgcggatc caaatatggg ttttgcttgt    300
cagttattac aatgccaaaa aagggttcat gcttctcctt tgagcccaag ttcattatta    360
aggatgtaca gagttgcacc tcattcacca tacgatcctt tgcatctcgt cccaaaaatg    420
ttaaatgatc cctcaccggc agcattagat tctagaggtg catttattat acacatacct    480
tcatcggtat atgtatggat tggtaagaaa tgtgaagcaa tc                       522

<210> SEQ ID NO 24
<211> LENGTH: 174
<212> TYPE: PRT
<213> ORGANISM: Lycopersicon esculentum

<400> SEQUENCE: 24

Asn Cys Val Gly Phe Val Cys Pro Glu Tyr Phe Lys Ser Asp Phe Val
 1               5                  10                  15

Tyr Arg Thr Leu Trp Leu Gln Asp Ser Pro Ser Glu Asp Ile Thr Ser
            20                  25                  30

Ile Leu Tyr Asp Val Phe Asp Tyr Phe Glu Asp Val Arg Glu Gln His
        35                  40                  45

Gly Lys Val Phe Val His Cys Cys Gln Gly Val Ser Arg Ser Thr Ser
    50                  55                  60

Leu Val Ile Ala Tyr Arg Met Trp Arg Glu Gly Gln Ser Phe Asp Asp
65                  70                  75                  80

Ala Phe Glu Tyr Val Lys Ala Ala Arg Gly Ile Ala Asp Pro Asn Met
                85                  90                  95

Gly Phe Ala Cys Gln Leu Leu Gln Cys Gln Lys Arg Val His Ala Ser
            100                 105                 110

Pro Leu Ser Pro Ser Ser Leu Leu Arg Met Tyr Arg Val Ala Pro His
        115                 120                 125

Ser Pro Tyr Asp Pro Leu His Leu Val Pro Lys Met Leu Asn Asp Pro
    130                 135                 140

Ser Pro Ala Ala Leu Asp Ser Arg Gly Ala Phe Ile Ile His Ile Pro
145                 150                 155                 160

Ser Ser Val Tyr Val Trp Ile Gly Lys Lys Cys Glu Ala Ile
                165                 170

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: degenerate
      primer
<221> NAME/KEY: misc_feature
<222> LOCATION: (1)..(21)
<223> OTHER INFORMATION: n = i

<400> SEQUENCE: 25
gcngcyttng crtcyttytc c                                              21

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: degenerate
      primer
<221> NAME/KEY: misc_feature
<222> LOCATION: (1)..(24)
```

```
<223> OTHER INFORMATION: n = i

<400> SEQUENCE: 26
ytcnckngcn ggnarrtgng tytc                                              24
```

MAP KINASE PHOSPHATASE MUTANT

This is a continuation of International Application No. PCT/EP99/05413, filed on Jul. 28, 1999, and published in English under PCT Article 21(2), the contents of which are incorporated herein by reference.

The present invention relates to DNA encoding proteins contributing to the regulation of a plant's response to abiotic stress and in particular genotoxic stress.

Cells of all organisms have evolved a series of DNA repair pathways which counteract the deleterious effects of DNA damage and are triggered by intricate signal cascades. To be able to modify or improve DNA repair using gene technology it is necessary to identify key proteins involved in said pathways or cascades. Therefore it is the main object of the present invention to provide DNA comprising an open reading frame encoding such a key protein.

DNA according to the present invention comprises an open reading frame encoding a protein characterized by a stretch of amino acids or component amino acid sequence having 40% or more identity with an aligned component sequence of SEQ ID NO: 3. The protein characterized by SEQ ID NO: 3 is tracked down with the help of a T-DNA tagged Arabidopsis mutant showing hypersensitivity to methyl methanesulfonate (MMS). Said hypersensitivity as well as an observed hypersensitivity to other DNA damaging treatments such as UV light is indicative of the proteins' involvement in the repair of DNA damage, or in signaling pathways implicated in the response to similar genotoxic stress. The mutant is also sensitive to elevated temperature and anti-oxidant N-acetylcysteine. The mutant is not sensitive to osmotic shock, increased salinity, oxidative stress or elevated ehtylene levels. An important characteristic of the mutant is cell death in response to growth in small closed vessels. This phenotype can be complemented by addition of abscisic acid (ABA) to the growth media. Furthermore, the mutant is more sensitive to exogenously applied ABA compared with the wild type which supports the notion that the genes disclosed by the present invention (SEQ ID NO: 1) are involved in stress signaling mediated by ABA.

Sequence alignments of SEQ ID NO: 3 using commercially available computer programs such as BLASTP of the NCBI BLAST family of programs or TFASTA or BestFit of the Wisconsin Package Software, all based on well known algorithms for sequence identity or similarity searches, reveal that stretches of SEQ ID NO: 3 (component sequences) having more than 100 and preferably between 120 to 250 amino acids length can show between 20% and almost 40% sequence identity to aligned stretches of known phosphatases, particularly phosphotyrosine phosphatases, MAP kinase phosphatases or dual specificity phosphatases. Protein phosphatases are classified by their substrate specificities as either phosphoserine/threonine phosphatases (PSTPs) or phosphotyrosine phosphatases (PTPs). The dual specificity phosphatases (DSPs) dephosphorylate both phosphotyrosine and phosphoserine/threonine residues and represent a subfamily of PTPs. MAP kinase phosphatases (MKPs) belong to the family of DSPs. The sequence VHCCQGVSRS (SEQ ID NO: 4) found in SEQ ID NO: 3 can be interpreted as corresponding to the mammalian sequence motif IHCXAGXXRS (SEQ ID NO: 5) defining the family of PTPs, wherein the Ile at the first position can be replaced by Val and the Ser at the last position can be replaced by Thr The present invention defines a new protein family the members of which are characterized by component amino acid sequences of more than 100 amino acid length showing 40% or higher amino acid sequence identity to aligned component sequences of SEQ ID NO: 3. Preferably said component sequences are of more than 120, more than 160 or even more than 200 amino acids length. The amino acid sequence identity is preferably higher than 50% or even higher than 55%. Most preferred are identities higher than 70%.

An example of DNA according to the present invention is described in SEQ ID NO: 1. The amino acid sequence of the protein encoded is identical to SEQ ID NO: 3. After alignment a stretch of the protein having about 140 amino acids shows 36% sequence identity to the MKP-1 protein described by Sun et al (Cell 75: 487–493, 1993). The identity determined after alignment with MKP-2 and MKP-3 is determined as 34% and 26%, respectively. Thus, according to the present invention a protein family related to MAP kinase phosphatases can be defined the members of which after alignment of a stretch of more than 100 amino acids length show 40% or higher amino acid sequence identity to SEQ ID NO: 3. Preferably, the amino acid sequence identity is higher than 50% or even higher than 55%. When making multiple sequence alignments, certain algorithms can take into account sequence similarities, such as same net charge or comparable hydrophobicity/hydrophilicity of the individual amino acids, in addition to sequence identities. The resulting values of sequence similarities, as compared to sequence identities, can help to assign a protein to the correct protein family in border-line cases. Proteins of particular interest, within the scope of the present invention, are MAP kinase phosphatases the amino acid sequence of which comprises at least one of the following characteristic amino acid subsequences:

(a) TSILYDFDYFEDV         (SEQ ID NO: 6)

(b) FVHCCQGVSRST         (SEQ ID NO: 7)

(c) FVHC         (SEQ ID NO: 8)

(d) QGVSRS         (SEQ ID NO: 9)

(e) YFKSD         (SEQ ID NO: 10)

DNA encoding proteins belonging to the new protein family according to the present invention can be isolated from monocotyledonous and dicotyledonous plants. Preferred sources are corn, sugar beet, sunflower, winter oilseed rape, soybean, cotton, wheat, rice, potato, broccoli, cauliflower, cabbage, cucumber, sweet corn, daikon, garden beans, lettuce, melon, pepper, squash, tomato, or watermelon. However, they can also be isolated from mammalian sources such as mouse or human tissues. The following general method, can be used, which the person skilled in the art will normally adapt to his specific task. A single stranded fragment of SEQ ID NO: 1 or SEQ ID NO: 2 consisting of at least 15, preferably 20 to 30 or even more than 100 consecutive nucleotides is used as a probe to screen a DNA library for clones hybridizing to said fragment. The factors to be observed for hybridization are described in Sambrook et al, Molecular cloning: A laboratory manual, Cold Spring Harbor Laboratory Press, chapters 9.47–9.57 and 11.45–11.49, 1989. Hybridizing clones are sequenced and DNA of clones comprising a complete coding region encoding a protein with more than 40% sequence identity to SEQ ID NO: 3 is purified. Said DNA can then be further processed by a number of routine recombinant DNA techniques such as restriction enzyme digestion, ligation, or polymerase chain reaction analysis.

The disclosure of SEQ ID NO: 1 enables a person skilled in the art to design oligonucleotides for polymerase chain reactions which attempt to amplify DNA fragments from templates comprising a sequence of nucleotides characterized by any continuous sequence of 15 and preferably 20 to 30 or more basepairs in SEQ ID NO: 1. Said nucleotides comprise a sequence of nucleotides which represents 15 and preferably 20 to 30 or more basepairs of SEQ ID NO: 1. Polymerase chain reactions performed using at least one such oligonucleotide and their amplification products constitute another embodiment of the present invention.

Knowing the nucleotide sequence of the Arabidopsis MKP1 gene and the amino acid sequence of the encoded protein it is possible to identify proteins interacting with AtMKP1 and to clone their corresponding genes using well known techniques. For example radioactively labeled AtMKP1 protein can be used for interactive cloning on cDNA expression libraries. AtMKP1 protein or parts thereof can be used to generate polyclonal or monoclonal antibodies specific for AtMKP1. The AtMKP1 gene can be used to generate variants of AtMKP1 protein tagged with GST, MYK or His. Said antibodies and MKP1 variants allow to isolate native protein complexes by immunoprecipitation and to determine sequences of proteins present in these complexes by micro-sequencing. The resulting sequence information can in turn be used to clone corresponding genes. Alternatively, said antibodies or tagged MKP1 variants can be used to screen epitope libraries for epitopes which interact with AtMKP1 protein. The AtMKP1 protein and parts thereof, in particular the N-terminal 490 amino acid region and the C-terminal 492 amino acid region can also be used to search for interacting proteins with a Two-hybrid system (e.g. in yeast, in mammalian cells, or in bacteria). This allows to obtain sequence information about interacting proteins.

Based on the disclosed finding that AtMKP1 proteins are involved in a plant's abiotic environmental stress response, it becomes possible to engineer the corresponding signaling pathway, of which AtMKP1 is a part, to be chemically regulated due to chemical activation or repression of transgenes encoding AtMKP1 or proteins interacting therewith. Such plants can be obtained by transformation with the corresponding genes under control of chemically inducible promoters. Application of inducers is expected to modify the activity of the AtMKP1 signaling pathway and to result in altered adaptation to abiotic environmental stress. Alternatively, AtMKP1 protein or its interacting proteins can be used as targets for chemicals inhibiting or stimulating their activities which again is expected to modify abiotic stress responses.

EXAMPLES

Example 1: Cloning of the Gene Responsible for the mkp1 Mutant Phenotype

Arabidopsis T-DNA insertion lines as produced by the INRA-Versailles and available from the Nottingham Arabidopsis Stock Center (NASC) are screened for sensitivity to methyl methanesulfonate (MMS) at a concentration of 100 ppm as described by Masson et al, Genetics 146: 401–407, 1997. Plants which die in the presence of 100 ppm MMS are found in the family AAN4. Thus, the corresponding T-DNA insertion mutation is assumed to give rise to this hypersensitive phenotype. This assumption is supported by genetic analysis showing co-segregation of the hypersensitive phenotype with the T-DNA insertion. Genomic DNA from the mutant plants is isolated as described by Dellaporta et al, Plant Mol Biol Reporter 1: 19–21, 1983. A fragment of genomic DNA flanking the right border of the inserted T-DNA is rescued essentially according to Bouchez et al, Plant Mol Biol Reporter 14: 115–123, 1996, with minor modifications. Genomic DNA is digested with PstI, ethanol precipitated and resuspended in $H_2O$. DNA of vector pResc38 (Bouchez et al supra) is digested with PstI and dephosphorylated with shrimp alkaline phosphatase. The phosphatase is heat inactivated, the vector DNA is ethanol precipitated and resuspended in $H_2O$. 2.5 µg of PstI digested genomic DNA and 2.5 µg of PstI digested and dephosphorylated vector are mixed and ligated overnight at room temperature in a total volume 100 µl in the presence of 10 units of T4 DNA ligase. The DNA of the ligation mixture is precipitated with ethanol, resuspended in 50 µl $H_2O$, and digested with XbaI in a total volume of 100 µl. XbaI digested DNA is precipitated with ethanol and resuspended in $H_2O$. A second overnight ligation reaction in the presence of 10 units T4 DNA ligase is performed in a total volume of 200 µl at room temperature to achieve circularization of DNA fragments. The DNA of the ligation mixture is again precipitated with ethanol, rinsed two times with 70% ethanol, dried and dissolved in 5 µl $H_2O$. Two 2 µl aliquots are used for electroporation of electrocompetent E. coli XL1-Blue cells (Stratagene) according to the manufacturer's instructions. Transformants containing the inserted T-DNA and adjacent Arabidopsis genomic DNA sequences are selected on plates with 50 mg/l kanamycin. Single bacterial colonies are analyzed by isolation of plasmid DNA using QIAprep Spin Plasmid Kit (Qiagen) and restriction digestion with PstI and XbaI. Plasmid pBN1 containing 3.7 kb of inserted T-DNA linked to 5 kb of Arabidopsis DNA is identified. Sequencing of the junction site is performed using a primer directed towards the flanking plant DNA and having the nucleotide sequence 5'-GGTTTCTACAGGACGTAACAT-3' (SEQ ID NO: 14) complementary to T-DNA 41 nucleotides from the right border. Digestion of this clone with SstI allows isolation of a 960 bp fragment which when labelled with $^{32}P$ can be conveniently used as a probe to screen wild type Arabidopsis genomic and cDNA libraries in order to identify the wild type gene affected in the mkp1 mutant line.

Example 2: Cloning of the AtMKP1 Wild-Type Gene

The 960 bp SstI fragment mentioned at the end of example 1 is labeled with $^{32}P$ by random oligonucleotide-primed synthesis (Feinberg et al, Anal Biochem 132: 6–13, 1983) for use as a probe in the following hybridization experiments.

Southern blot analysis of Arabidopsis wild type and mkp1 DNA digested with EcoRV confirms that in the mkp1 genomic DNA the sequence hybridizing to the probe is linked to T-DNA.

Northern blot analysis of Arabidopsis wild type RNA reveals the presence of a hybridizing transcript in RNA extracted from seven-day-old wild type seedlings. No such hybridizing fragment is detected in the corresponding RNA of mkp1 seedlings.

A cDNA library (Elledge et al, 1991) and a genomic library (Stratagene) of wild type Arabidopsis thaliana ecotype Columbia is screened with the labelled SstI fragment mentioned above. Screening of the bacteriophage λ libraries is performed according to the protocols described in chapter 6 of Ausubel et al, 1994, "Current protocols in molecular biology", John Wiley & Sons, Inc. Hybridization is performed as described by Church and Gilbert, Proc Natl Acad Sci USA 81: 1991–1995, 1984. Bacteriophage clones hybridizing to SstI fragment are subjected to in vivo excision of plasmids according to Elledge et al, Proc Natl Acad Sci USA 88: 1731–1735, 1991, and Stratagene protocols. Inserts of the plasmids obtained are further analyzed by sequencing.

By partial sequencing and alignment of ten overlapping clones (pBN5.1 to pBN5.10) isolated from the genomic library a continuous genomic sequence of 6356 bp (see SEQ ID NO: 1) is decoded.

Ten cDNA clones representing the same gene, one of them a 3.0 kb full-length cDNA (SEQ ID NO: 2), are isolated from the cDNA library.

Example 3: Sequence Analysis and Alignments

The 3 kb full-length cDNA clone of SEQ ID NO: 2 encodes an ORF with the start codon being defined by basepairs 298–300 and the stop codon by basepairs 2650–2652. The ORF encodes a protein consisting of 784 amino acids (SEQ ID NO: 3) and a predicted molecular mass of 86.0 kD. Alignment with the genomic sequence of SEQ ID NO: 1 reveals three introns. T-DNA is inserted within the coding sequence of the mkp1 mutant DNA before basepair position 502 according to the numbering of SEQ ID NO: 2. The sub-sequence VHCCQGVSRS (SEQ ID NO: 4) found in SEQ ID NO: 3 can be interpreted as corresponding to the mammalian sequence motif IHCXAGXXRS (SEQ ID NO: 5) defining the family of protein tyrosine phosphatases, wherein the Ile at the first position can be replaced by Val and the Ser at the last position can be replaced by Thr (Van Vactor et al, Curr Opin Gen Dev 8:112–126, 1998). Therefore it is concluded that the wild type ORF encodes a protein tyrosine phosphatase with invariant aspartic acid, cysteine, and arginine residues (Fauman et al, Trends Biochem Sci 21: 413–417, 1996) in positions 204, 235 and 241 according to SEQ ID NO: 3.

A data base search using the TFASTA program (Wisconsin Package Version 9.1, Genetics Computer Group (GCG), Madison, Wis.) reveals that the encoded phosphatase has a significant similarity to dual specificity phosphatases. The closest homologue identified is *Xenopus laevis* MAP kinase phosphatase (MKP; Lewis et al, J Cell Sci 108: 2885–2896, 1995) showing 38.1% identity and 52.5% similarity in a 140 amino acid overlap region. The deduced AtMKP1 protein also has 36.0% identity and 52.5% similarity with a 140 amino acid overlap region encoded by the rat 3CH134/CL100 cDNA representing a rat MKP1. Essentially identical results are obtained when using the BLASTP 2.0.4 (Feb. 24, 1998) program of the NCBI BLAST family of programs which, allowing gapped alignment, compares an amino acid query sequence against a protein sequence database (Altschul et al, Nucleic Acids Res. 25: 3389–3402, 1997). No higher plant homologues are identified. The genomic position of the AtMKP1 gene is determined by hybridization to filters containing genomic YAC clones publicly available from the Arabidopsis Biological Resource Center (Ohio, USA). The AtMKP1 gene is found to map to chromosome 3 between markers ve022 and BGL1.

Example 4: Complementation mkp1 mutant plants are transformed with DNA comprising the corresponding wild type genomic DNA including promoter and polyadenylation signal to find out whether the cloned wild type gene is able to complement the mutant mkp1 phenotype.

mkp1 mutant plants harbor T-DNA containing the NPTII and bar marker genes under the control of nos and CaMV35S promoters, respectively. Therefore, different marker genes are used for the transformation construct. The vector used is a derivative of p1'barbi which is highly efficient in Arabidopsis transformation (Mengiste et al, Plant J 12: 945–948, 1997). In p1'barbi the EcoRI fragment containing 1'promoter, bargene coding region, and CaMV 35S polyadenylation signal is inverted in respect to the T-DNA borders by EcoRI digestion and re-ligation. In the resulting plasmid the 1'promoter (Velten et al, EMBO J 3: 2723–2730, 1984) is directed towards the right border of the T-DNA. This plasmid is digested with BamHI and NheI, and the bar gene and CaMV 35S polyadenylation signal are replaced by a synthetic polylinker with the sites for the restriction enzymes BamHI, HpaI, ClaI, StuI and NheI. The resulting plasmid is digested with BamHI and HpaI and ligated to a BamHI-PvuII fragment of pROB1 (Bilang et al, Gene 100: 247–250, 1991) containing the hygromycin-B-resistance gene hph linked to the CaMV 35S polyadenylation signal. The T-DNA of the resulting binary vector p1'hygi contains the hygromycin resistance selectable marker gene under the control of the 1'promoter and unique cloning sites for the restriction enzymes ClaI, StuI and NheI located between the marker gene and the T-DNA right border. p1'hygi is used to insert the reconstructed AtMKP1 gene as follows. Plasmid pBN1 of example 1 is digested with PstI and MunI and dephosphorylated. The restriction fragment containing the 3'portion of the AtMKP1 gene and pBluescript-SK(+) is purified from the agarose gel and ligated to the PstI-MunI restriction fragment of the wild type genomic clone pBN5.2 (example 2) including the 5' end of the coding sequence of the AtMKP1 gene and 2.4 kb of upstream sequences. The reconstructed AtMKP1 gene is excised by PstI and NotI and after filling the ends is inserted into the StuI site of p1'hygi. The construct is introduced by transformation into *Agrobacterium tumefaciens* strain C58ClRif$^R$ containing the non-oncogenic Ti plasmid pGV3101 (Van Larebeke et al, Nature 252: 169–170, 1974). T-DNA containing the reconstructed AtMKP1 gene is transferred to mutant plants by the method of in planta Agrobacterium mediated gene transfer (Bechtold et al, C R Acad Sci Paris, Life Sci 316: 1194–1199, 1993). Seeds of infiltrated plants are grown on hygromycin-containing medium to screen for transformants. The progeny of selfed hygromycin resistant plants is analyzed for the segregation of hygromycin resistance. The families in which a 3:1 segregation ratio is observed are used to isolate homozygous lines bearing the newly introduced T-DNA inserted at a single genetic locus. The obtained hygromycin resistant lines are analyzed by Northern blot analysis for the restoration of AtMKP1 expression. In these lines the restoration of transcription of the AtMKP1 gene can be observed as well as the restoration of the wild type level of MMS resistance and ABA mediated stress responses. Complementation is not observed in plants transformed with p1'hygi only.

Example 5: Cloning of Homologous Sequences from Other Plant Species

Use of AtMKP1 cDNA as a probe for Southern hybridization with genomic DNA from other plant species such as *Sinapis alba* (mustard), *Lycopersicum esculentum* (tomato) and *Zea mays* (maize) is successful in the case of Sinapis alba which belongs to the same family as Arabidopsis (Brassicaceae).

Homologous sequences from the other species can be identified in a PCR approach using degenerate primers 1–3 below, wherein I is inosine, derived from the regions conserved between VH-PTP13 of *Clamydomonas eugametos* and AtMKP1 protein:

```
Primer 1 (forward): 5'-AAY AAY GGI ATH ACI CAY ATH YT-3';  (SEQ ID NO: 11)

Primer 2 (reverse): 5'-YTG RCA IGC RAA ICC CAT RTT IGG-3'; (SEQ ID NO: 12)

Primer 3 (reverse): 5'-IGT CCA CAT IAR RTA IGC DAT IAC;    (SEQ ID NO: 13)
```

A PCR reaction is performed in a total volume of 50 μl containing 1×reaction buffer (Qiagen), 200 μM of each dNTP, 1.25 units of Taq polymerase (Qiagen), and 100 pmol of each primer.

Reaction 1 is performed with primers 1 and 2 using genomic DNA from *Sinapis alba* (200 ng), *Lycopersicum esculentum* (400 ng), or *Zea mays* (600 ng) as the original template DNA. Amplification is carried out after an initial denaturation step of 3 min at 94° C., followed by 30 cycles of 30 sec at 94° C., 30 sec at 40° C., and 3 min at 72° C. The resulting amplification mixture is diluted $10^3$ fold.

Reaction 2 is performed using 2 μl of the above dilution to provide the necessary template DNA. This time primers 1 and 3 are used under the same conditions as specified for reaction 1. The resulting amplification products are cloned into the T/A vector pCR2.1 (Invitrogen) and further analyzed by nucleotide sequencing.

Using this PCR approach it is possible to amplify sequences homologous to the AtMKP1 gene from all the species mentioned above. Whereas the nucleotide sequence from *Sinapis alba* SaMKP1 ((SEQ ID NO: 15 encoding SEQ ID NO: 16) is 90.8% identical to the AtMKP1 sequence, the nucleotide sequence from *Lycopersicum esculentum* LeMKP1 (SEQ ID NO: 17 encoding SEQ ID NO: 18) is 72.3% and the *Zea mays* sequence ZmMKP1 (SEQ ID NO: 19 encoding SEQ ID NO: 20) 71.8% identical. The fragments hybridize to genomic DNA from corresponding species under the usual hybridization conditions for Southern blot analysis. The fragments can be used as probes to screen cDNA libraries for corresponding cDNA sequences.

The 243 bp ZmMKP1 fragment amplifying from maize DNA is used as a probe to screen a maize cDNA library (Clontech) made in the Lambda ZAP®II Vector (Clontech) from "Blizzard" hybrid etiolated shoots, which were treated with the herbicide safener Benoxacor. The titer of the library is determined as $3 \times 10^9$ pfu/ml.

Library screening is conducted as described in the Clontech Lambda Library Protocol Handbook, with some slight modifications. Briefly, a single colony of XL-1 Blue is picked and incubated overnight at 37° C. in LB medium, containing 10 mM $MgSO_4$ and 0.2% maltose. 600 μl of stationary phase grown bacteria for each 150 mm plate is combined with 100 μl of phage library dilution in sterile 1×lambda dilution buffer (100 mM NaCl; 10 mM $MgSo_4$; 35 mM Tris-HCl, pH7.5) to yield approximately 30,000 pfu per plate. This mixture is incubated at 37° C. for 15 minutes, subsequently 7 ml of melted LB soft top agarose (at 48° C.) is added to the cell suspension for each 150 mm plate, shortly mixed and then poured on two-day-old $LB^{MgSO4}$ agar plates, which have been pre-warmed to 37° C. for four hours. The plates are then incubated at 37° C. until plaques reach appropriate sizes (after about 8 to 9 hours). After chilling the plates at 4° C. for one hour, phage particles are transferred to Hybond N nitrocellulose filters and the orientation of each filter to its plate is recorded with a waterproof pen. The filters are then treated by placing them on Whatman 3MM paper saturated with the appropriate solution. The treatments include denaturation solution (0.5M NaOH; 1.5M NaCl) for 2 minutes, followed by neutralization solution (0.5M Tris-HCl, pH 7.2; 1.5M NaCl; 1 mM EDTA) for 3 minutes and 2×SSC for 3 minutes. DNA is subsequently crosslinked to the filters by UV.

Filters are then pre-hybridized, hybridized with the radioactivelly labeled ZmMKP1 fragment and washed as described in Sambrook et al, Molecular cloning: A laboratory manual, Cold Spring Harbor Laboratory Press, chapters 9.47–9.57 and 11.45–11.49, 1989. An agar plug from the position of a positive plaque is then removed from the master plate and incubated overnight at 4° C. in 1 ml of 1×lambda dilution buffer, containing 20 μl of chloroform. Each titer is determined and the phages are re-plated to obtain approximately 200 to 500 plaques on a 150 mm plate for a secondary screen as described above. Single plaques of interest are collected from the agar plates and incubated overnight at 4° C. in 500 μl of 1×lambda dilution buffer and 20 μl of chloroform.

The pBluescript phagemid is excised from the λZAP™ vector as described by the In Vivo Excision Protocol using the ExAssisVSOLR System in the Stratagene Uni-ZAP™ XR Library Instruction Manual (1993). A $\frac{1}{100}$ dilution is made of XL1-Blue MRF' and SOLR overnight cultures (at 30° C.) and incubated at 37° C. for 2–3 hours. XL1-Blue MRF' cells are then pelleted for 10 minutes at 1,500×g and re-suspended at an $OD_{600}=1.0$ in 10 mM $MgSO_4$. 200 μl of these XL1-Blue cells are then combined with 250 μl of phage stock and 1 μl of ExAssist helper phage in a 50 ml conical tube and incubated at 37° C. for 15 minutes. 3 ml of LB broth is added and incubated at 37° C. for 5 hours, after which the cells are pelleted for 15 minutes at 2,000×g and the supernatant transferred to a new tube. The tube is then heated at 70° C. for 15 minutes and centrifuged again for 15 minutes at 4,000×g. The supernatant, containing the excised phagemid pBluescript packaged as filamentous phage particles, is decanted into a new tube. 10 and 100 μl of this phage stock are then added to two tubes with 200 μl of SOLR cells that have been allowed to grow to $OD_{600}=$ 0.5–1.0 before being removed from the incubator and further incubated at room temperature. The tubes are incubated at 37° C. for 15 minutes, followed by plating 10–50 μl from each tube on $LB^{amp}$ (50 μg/ml) and over night incubation at 37° C.

The positive clones are checked for insert size by EcoRl/Xhol double digestion and end-sequencing with T3 and T7 promoter primers (Promega).

Screening of 360,000 pfu of the library results in three identical clones of 2.2 kb containing the 3' poly(A) tail, but lacking part of the 5' end, including the translation initiation site. The gene corresponding to the identified partial cDNA clone is named ZmMKP2, as it is not identical with the ZmMKP1 fragment used as the probe (92.3% identity on the nucleotide level over the 196 bp fragment flanked by the primers 1 and 3). An additional 213 nucleotides are amplified and cloned by 5' RACE (rapid amplification of cDNA ends) carried out following the instructions of the 5'/3' RACE Kit (Boehringer Mannheim) resulting in a longer cDNA sequence of 2,452 bp but still not complete, judged by the predicted mRNA length from the RNA gel blot analysis and the absence of a possible translation initiation site. The sequence information gained from the ZmMKP2 cDNA including the additional 213 nucleotides obtained by 5' RACE (SEQ ID NO: 21 encoding SEQ ID NO: 22) is used to design two additional backward oriented degenerate primers wherein I is inosine to 3' regions conserved between the deduced peptide sequences of ZmMKP2 and AtMKP1:

```
Primer 4 (reverse): 5'-GCI GCY TTI GCR TCY TTY TCC-3';    (SEQ ID NO: 25)

Primer 5 (reverse): 5'-YTC ICK IGC IGC IAR RTG IGT YTC-3' (SEQ ID NO: 26)
```

These primers are used to PCR amplify a larger fragment of a MAP kinase phosphatase gene from tomato. The amplified and cloned 522 bp long fragment is not identical to LeMKP1. Therefore, its corresponding gene is named LeMKP2 (SEQ ID NO: 23 encoding SEQ NO: 24; 75% identity on the nucleotide level over the stretch of 196 bp of ZmMKP1 flanked by primers 1 and 3). The origins of all identified MAP kinase phosphatase homologous gene sequences are confirmed by Southern blot analysis.

The following Table shows an alignment of a continuous stretch of 312 amino acids of AtMKP1 with the related amino acid sequence of ZmMKP2.

```
AtMKP1 139 KREKIAFFDKECSKVADHIYVGGDAVAKDKSILKNNGITHILNCVGFICP 188
           :::.||||||||||||||:|.||||||.: ||: |||||:||||||:||
ZmMKP2  24 RKDQIAFFDKECSKVADHVYLGGDAVAKNRDILRKNGITHVLNCVGFVCP  73

AtMKP1 189 EYFKSDFCYRSLWLQDSPSEDITSILYDVFDYFEDVREQSGRIFVHCCQG 238
           ||||||  ||.|||||||.|||||||||||||||||||||  ||: ||||||
ZmMKP2  74 EYFKSDLVYRTLWLQDSPTEDITSILYDVFDYFEDVREQGGRVLVHCCQG 123

AtMKP1 239 VSRSTSLVIAYLMWREGQSFDDAFQYVKSARGIADPNMGFACQLLQCQKR 288
           |||||||||||||||||||||||||:||.|||||.|||||||||||||||
ZmMKP2 124 VSRSTSLVIAYLMWREGQSFDDAFQFVKAARGIANPNMGFACQLLQCQKR 173

AtMKP1 289 VHAFPLSPTSLLRMYKMSPHSPYDPLHLVPKLLNDPCPGSLDSRGAFIIQ 338
           ||| |||| |.||||:|.||| | ||||||||:|||| | .||||||||:
ZmMKP2 174 VHAIPLSPNSVLRMYRMAPHSQYAPLHLVPKMLNDPSPATLDSRGAFIVH 223

AtMKP1 339 LPSAIYIWVGRQCETIMEKDAKAAVCQIARYEKVEAPIMVVREGDEPVYY 388
           . |.:|:||| .|: :|||||||||  |: |||||:  | ||||| ||  :
ZmMKP2 224 VLSSLYVWVGMKCDPVMEKDAKAAAFQVVRYEKVQGHIKVVRBGLEPQEF 273

AtMKP1 389 WDAFASILPMIGG..........SVIKVQPGDRKVDAYNLDFEIFQKAIE 428
           ||||.|. |           |   || || :.|. |||: |||
ZmMKP2 274 WDAFSSMPPNSDSNTKISKDQIDSASKSDPGSRKNESYDADFELVYKATT 323

AtMKP1 429 GGFVPTLASSNNEHETHLPARE                             450
           || ||  ..|    |||||||||.
ZmMKP2 324 GGVVPAFSTSGAGDETHLPARE                             345
```

What is claimed is:

1. An isolated DNA comprising an open reading frame encoding a phosphatase protein contributing to repair of DNA damage in a plant cell, wherein said phosphatase protein is characterized by a component amino acid sequence having about 70% or more identity with an aligned component sequence of SEQ ID NO:3.

2. The DNA according to claim 1, wherein said phosphatase protein is a dual specificity phosphatase derivable from a plant.

3. The DNA according to claim 1 wherein the open reading frame encodes a protein comprising at least one component amino acid sequence chosen from SEQ ID NO:4, SEQ ID NO:6, SEQ ID NO:7, SEQ ID NO:8, SEQ ID NO:9, and SEQ ID NO:10.

4. The DNA according to claim 1, wherein the open reading frame encodes a protein characterized by the amino acid sequence of SEQ ID NO:3.

5. The DNA according to claim 1 characterized by the nucleotide sequence of SEQ ID NO:1.

6. The DNA according to claim 1 wherein the open reading frame encodes a protein conferring hypersensitivity to treatment with methyl methanesulfonate (MMS).

7. The DNA according to claim 1 wherein the open reading frame encodes a protein conferring hypersensitivity to treatment with UV light or X-rays.

8. The DNA according to claim 1, wherein said protein interferes with abscisic acid signal transduction.

9. An isolated DNA encoding a phosphatase protein, wherein said phosphatase protein comprises a component amino acid sequence having at least about 70% identity with an aligned component sequence of SEQ ID NO:3, and wherein said component amino acid sequence comprises at least one sequence motif chosen from SEQ ID NO:4, SEQ ID NO:6, SEQ ID NO:7, SEQ ID NO:8, SEQ ID NO:9, and SEQ ID NO:10.

10. The DNA of claim 9, wherein said isolated DNA is derivable from a plant.

11. The DNA of claim 9, wherein said phosphatase protein is a dual specificity phosphatase.

12. The DNA of claim 11, wherein said phosphatase protein is a MAP kinase phosphatase.

13. The DNA of claim 9, wherein said phosphatase protein is characterized by an amino acid sequence shown in SEQ ID NO:3.

14. The DNA of claim 9, wherein said isolated DNA is characterized by a nueleotide sequence shown in SEQ ID NO:1.

* * * * *